US009512460B2

(12) United States Patent
Mayer et al.

(10) Patent No.: US 9,512,460 B2
(45) Date of Patent: Dec. 6, 2016

(54) METHOD OF STUDYING A CRYOGENIC SAMPLE IN AN OPTICAL MICROSCOPE

(71) Applicant: FEI Company, Hillsboro, OR (US)

(72) Inventors: Tobias Mayer, Krailling (DE); Rainer Daum, Wessling (DE); Matthias Geisbauer, Karlsfeld (DE); Rudolf Johannes Peter Gerardus Schampers, Tegelen (NL); Johannes Antonius Hendricus Wilhelmus Gerardus Persoon, Waalre (NL)

(73) Assignee: FEI COMPANY, Hillsboro, OR (US)

( * ) Notice: Subject to any disclaimer, the term of this patent is extended or adjusted under 35 U.S.C. 154(b) by 34 days.

(21) Appl. No.: 14/196,178

(22) Filed: Mar. 4, 2014

(65) Prior Publication Data

US 2014/0248649 A1    Sep. 4, 2014

(30) Foreign Application Priority Data

Mar. 4, 2013  (EP) .................................. 13157564

(51) Int. Cl.
  G02B 21/28    (2006.01)
  C12Q 1/02     (2006.01)
  G02B 27/00    (2006.01)

(52) U.S. Cl.
  CPC ................. *C12Q 1/02* (2013.01); *G02B 21/28* (2013.01); *G02B 27/0006* (2013.01)

(58) Field of Classification Search
  CPC .. C12Q 1/02; C12Q 1/686; C12Q 2565/119; C12Q 1/6869; C12Q 2527/125; C12Q 2547/101; C12Q 2565/301; C12Q 2565/537; C12Q 1/6844; C12Q 2525/186; C12Q 2531/113; C12Q 2565/629; C12Q 1/68; C12Q 1/6834; C12Q 1/6865; G02B 21/28; G02B 27/0006
  USPC ............ 359/368, 395, 398, 900; 356/36, 38, 356/437, 440, 244
  See application file for complete search history.

(56) References Cited

U.S. PATENT DOCUMENTS

| | | | |
|---|---|---|---|
| 4,364,630 A * | 12/1982 | Hayasaka | ...................... 359/379 |
| 6,233,093 B1 * | 5/2001 | Arnold et al. | ................ 359/395 |
| 6,758,362 B2 | 7/2004 | Studer | |
| 7,413,872 B2 | 8/2008 | Frederik et al. | |
| 8,144,406 B2 | 3/2012 | Wadell et al. | |
| 2007/0289307 A1 * | 12/2007 | Grote et al. | ..................... 60/753 |
| 2010/0102248 A1 * | 4/2010 | Milas et al. | ............. 250/440.11 |
| 2012/0154934 A1 | 6/2012 | Wadell et al. | |

FOREIGN PATENT DOCUMENTS

| | | |
|---|---|---|
| JP | 3096038 | 10/2000 |
| JP | 2007-052387 | 3/2007 |
| JP | 2011180375 | 9/2011 |

OTHER PUBLICATIONS

Unknown, 'Optical Microscope,' website: http://en.wikipedia.org/wiki/Light_microscope, obtained Mar. 4, 2014, 8 pages.
Unknown, 'Inverted Microscope,' website: http://en.wikipedia.org/wiki/Inverted_microscope, obtained Mar. 4, 2014, 1 page.
Unknown, 'Glass Transition,' website: http://en.wikipedia.org/wiki/Glass_transition, obtained Mar. 4, 2014, 6 pages.
Unknown, 'Cryogenics,' website: http://en.wikipedia.org/wiki/Cryogenics, obtained Mar. 4, 2014, 3 pages.
Unknown, 'Thermoelectric Cooling,' website: http://en.wikipedia.org/wiki/Thermoelectric_cooling, obtained Mar. 4, 2014, 3 pages.
Unknown, 'Reynolds Number,' website: http://en.wikipedia.org/wiki/Reynolds_number, obtained Mar. 4, 2014, 6 pages.

* cited by examiner

*Primary Examiner* — Bumsuk Won
*Assistant Examiner* — Henry Duong
(74) *Attorney, Agent, or Firm* — Scheinberg & Associates, P.C.; John Kelly; Michael O. Scheinberg (57) ABSTRACT

The present invention relates to a method of studying a sample using an optical microscope, comprising providing the sample in a sample holder with means to maintain the sample at a temperature below 273 K; providing a microscope objective lens, in a thermally insulating jacket, having an extremal lens element proximal to the sample holder; bringing the lens into a focus position proximal to the sample, which separates the extremal lens element and sample by an intervening space, providing a transparent window in said intervening space, with a gap between the window and the extremal lens element; providing a flow of substantially dry gas in said gap; and tailoring the geometry and velocity of said flow so that, at least in said gap, the flow is non-laminar; and does not excite substantial acoustic vibration in a structure proximal the gap.

17 Claims, 4 Drawing Sheets

METHOD OF STUDYING A CRYOGENIC SAMPLE IN AN OPTICAL MICROSCOPE

The invention relates to a method of studying a sample using an optical microscope, comprising the following steps:
  Providing the sample in a sample holder comprising means to maintain the sample at a temperature T below 273 K;
  Providing a microscope objective lens having an extremal lens element proximal the sample holder;
  Bringing the lens into a focus position proximal the sample, the extremal lens element and sample being separated by an intervening space,
The invention also relates to an optical microscope in which such a method can be performed.

For purposes of clarity and consistency, the following terms as used throughout this text and the appended claims should be interpreted as follows:
  The term "microscope" refers to an apparatus that is used to create a magnified image of an object, feature or component that is generally too small to be seen in satisfactory detail with the naked human eye. An "optical" microscope performs such imaging using optical wavelengths of light, i.e. visible wavelengths, as well as near infrared and near ultraviolet wavelengths. It may, for example, be of an "inverted type" (where a sample under investigation is located (substantially) above the objective lens) or of a "standard type" (in which the sample is located (substantially) below the objective lens). The term "optical microscope" should be broadly interpreted as encompassing devices such as fluorescence microscopes, for example.
  The term "objective lens" is intended to refer to an optical assembly disposed proximal the sample and used to form an image thereof. This image may, for example, be viewed through an ocular using the naked eye, or using a camera. In general, an objective lens in a microscope will be a compound lens, comprising a plurality of refractive elements arranged along an optical axis and mounted within a (tubular) housing, which is often metallic; one of these refractive elements can be designated as "extremal lens element", being the refractive element closest to the sample holder (furthest from the ocular/camera). Typically, several such objective lenses (e.g. of different optical powers) will be disposed on a turret/carrousel arrangement—or other exchanging device, such as a slider arrangement—that will allow a user of the microscope to view the sample though a selection of different objectives. The refractive elements of the objective lens will generally comprise a material such as quartz, pure glass, doped glass (e.g. flint glass, crown glass), etc., though they may also conceivably comprise other materials, such as crystalline ionic compounds (e.g. calcium fluoride) or transparent polymers, such as PMMA. In the case of a compound lens, not all constituent lens elements necessarily have to have the same constitution.
  The term "focus position" should be interpreted as referring to a situation whereby at least a portion of the sample is located within a focal plane of the objective lens. The relative spacing of the sample and objective lens is generally adjustable, so as to facilitate attainment/adjustment of this focus position. The lens may be "brought into" a desired focus position by appropriately adjusting the position of at least one of the sample holder and the objective lens.

These points will be discussed in more detail below.

Optical microscopes are very familiar instruments that enjoy widespread application in a variety of fields, such as biology, mineralogy, materials science, forensics, semiconductor manufacturing, etc. In many cases, the sample holder in such a microscope is a relatively simple construction, and basically comprises a platform that can be positioned in various degrees of freedom and that is provided with a clamping mechanism (such as one or more sprung clips) to hold a sample (typically mounted on or between microscope slides) on a surface facing the objective lens. Such an arrangement will generally be satisfactory for typical sample investigations at room temperature (ca. 300 K). However, there are many situations in which it is desirable to maintain a sample at sub-zero temperatures (below ca. 273 K) while it is being studied with an optical microscope; for example, one may be interested in performing investigations at temperatures at or around the glass transition temperature/vitrification temperature of water (136 K), or one may want to examine phenomena at so-called "cryogenic temperatures" (i.e. below ca. 123 K). This may be because the sample involved may only demonstrate a particular behavior at low temperatures (e.g. a particular phase, crystalline state, conductivity, fluidity, bond formation, etc.), or it may be necessary to keep the sample frozen for purposes of preservation (e.g. as with biological samples taken from permafrost, for example). In such cases, the sample holder will need to comprise (supplementary) means for maintaining the sample at low temperatures, e.g. a cooling conduit in thermal contact with the sample and through which a suitable coolant (such as liquid nitrogen or liquid helium) can be passed, or a Peltier element, for example. In the case of an inverted microscope, the sample may, for example, be located at the bottom of a chamber in such a manner as to be in intimate thermal contact with a body of liquid coolant (such as liquid nitrogen or helium); in such a case, the sample can be viewed through a transparent bottom wall (portion) of the chamber.

As a specific example of the usefulness of conducting studies at low temperatures, reference is made to biological samples that are frozen so as to arrest a specimen in a given state. The formation of ice crystals during the freezing process should be avoided, as such crystals tend to damage certain structures in the sample, e.g. by puncturing cell membranes. Crystallization can be avoided by flash-freezing the sample to a temperature below the glass transition temperature of water, using an ultra-high cooling rate (e.g. of the order of 105 K/s) and possibly also high pressure (e.g. 2000 bar). Such techniques are known per se, and are, for example, described in U.S. Pat. No. 7,413,872 and U.S. Pat. No. 6,758,362 B2 (incorporated herein by reference). A further advantage of working at such low temperatures is that so-called "photo-bleaching" (i.e. a diminishing response of fluorescent markers to probing light) tends to be less pronounced at very low temperatures than at room temperature.

Viewing samples at sub-zero temperatures using an optical microscope is hampered by problems. One of these concerns the fact that, when an objective lens is proximal the sample—with only a small intervening space in between (typically of the order of a millimeter or less)—at least a portion of the objective lens nearest to the sample will tend to become strongly cooled (since the sample will act as a heat sink). One disadvantage of this is that moisture present in said intervening space will tend to condense on (parts of) the objective lens, with generally very disadvantageous consequences as regards optical performance (image distortion due to droplet/ice formation), corrosion (due to rust), degradation of optical coatings, etc. Another disadvantage concerns the fact that refractive index and various optical aberrations are a function of temperature; consequently, changing the temperature of the objective lens—and, in particular, introducing a (strong) temperature gradient along that lens—will tend to adversely affect the imaging performance of the lens (as regards optical resolution and/or aberrations).

Theoretically, there are various ways in which to try to address these problems. For example:

(i) One could arrange an enclosure to encapsulate (at least) the objective lens and the sample, and could try to ensure that this enclosure is substantially free of humidity, e.g. by filling it with a dry gas and/or by using a dessicating agent therein (such as silica gel). However, although this solution might address the issue of condensation, it would not address the issue of temperature change/gradient in the objective lens.

(ii) With reference to the enclosure in (i), one could try to cool the entire interior of the enclosure (not just the sample holder) to the desired temperature of the sample; this way, the whole objective lens is at the same temperature as the sample, and the temperature gradient alluded to above is removed. However, as already stated above, refractive index (of refractive materials and intervening air spaces) and various optical aberrations are a function of temperature, and a particular optical design will generally only work satisfactorily in a relatively narrow temperature range. Consequently, an objective lens designed for room-temperature use will often give sub-optimal imaging results at sub-zero temperatures and, as a result, a separate optical design will have to be developed for low-temperature use. This increases costs and reduces flexibility of microscope design and implementation.

(iii) A problem with a static gas environment in the (vicinity of the) intervening space between the sample and the objective lens is that such a set-up generally does not optimally combat the above-mentioned condensation problem. This is because any pocket of moisture that does manage to work its way into said space (e.g. by Brownian motion, or a draft) will be able to condense unhindered onto the lens and/or the sample. To combat this problem, one could contemplate use of a moving gas stream that runs through said space and that serves to carry away any molecules of water vapor that may get into the enclosure. However, purging such an enclosure in this manner would tend to use up a relatively large quantity of relatively expensive purge gas, leading to a substantial increase in operating costs.

It is an object of the invention to address these issues. More specifically, it is an object of the invention to provide a satisfactory method/apparatus whereby an optical microscope can be used to study a sample at a temperature T<273 K, and especially T<136 K. In particular, it is an object of the invention that such a method/apparatus should not be impeded by significant condensation/ice formation on (parts of) an objective lens of the microscope. Moreover, it is an object of the invention that the method/apparatus in question should not involve said objective lens being subjected to a substantial temperature change during use.

These and other objects are achieved in a method as specified in the opening paragraph, characterized by the following steps:
  Providing the objective lens in a thermally insulating jacket;
  Providing a transparent window in said intervening space, with a gap between the window and the extremal lens element;
  Providing a flow of substantially dry gas in said gap;
  Tailoring the geometry and velocity of said flow so that, at least in said gap, the flow:
    Is non-laminar;
    Does not excite substantial acoustic vibration in a structure proximal the gap.

The invention has a number of key elements that combine synergistically to produce a satisfactory end result. These can be explained as follows:
  The objective lens is placed in a thermally insulating jacket in order to shield it from the relatively low temperature of the sample, thus serving to keep the lens at the operating temperature for which it was designed, and helping to prevent troublesome temperature gradients along the lens.
  The transparent window between the extremal lens element ("ELE") and the sample forms a further thermal shield that protects the relatively warm objective lens (heat source) from the relatively cold environment of the sample (heat sink).
  The intervening space (so-called "working distance") between the ELE and the sample is typically very small, e.g. of the order of about a millimeter. Necessarily, the gap between the window and the ELE is even smaller. As a result, purging this gap with dry gas requires only a relatively small quantity of gas (per unit of time), thus substantially reducing operating costs. Because a flow of gas is chosen rather than a static volume of gas, any molecules of water vapor present in the gap will tend to be swept away by the flow.
  The inventors observed that the efficiency with which water vapor is swept away by the gas flow increases if the flow is turbulent rather than laminar. Such a turbulent flow has a "churning" effect that tends to eliminate dead zones/static boundary layers in the gap, thus more effectively removing potential "nests" of water vapor.
  On the other hand, if the gas flow in the gap is too turbulent, the inventors observed that the imaging performance of the microscope deteriorates. Initially, it was thought that this might be due to excessive density differences in the turbulent gas in the gap, with the attendant differences in refractive index of the gas causing distortion of the microscope image. Another avenue of investigation considered by the inventors involved the possibility that excessive turbulence in the gas was resulting in a large gas pressure on one side of the window, causing it to deform from an initial optically flat form into a slightly distended/meniscus-shaped form, thus introducing parasitic refractive power. However, closer analysis led to both of these possibilities being discounted as substantial causes of the observed imaging deterioration. Finally, after much further investigation, the inventors demonstrated that the imaging degradation was being caused by relatively high-frequency, fine acoustic vibrations in the window, which were being excited by the overly turbulent gas in the gap; put another way, the window was "singing" in response to resonant stimulation by the gas, and the associated fine vibration of the window was causing it to demonstrate unwanted refractive power. Further investigation revealed that similar vibration could be induced in the sample and/or sample holder, with attendant blurring of the microscope image. Sure enough, when the degree of turbulence in the gas was reduced to lower levels (still non-laminar), such vibration stopped, and imaging performance of the microscope returned to normal.

The skilled artisan will realize that flow behavior of a fluid (gas or liquid) in a channel can be described with the aid of various dimensionless "characteristic numbers", and particularly by Reynolds number Re=ρvL/μ, which considers key physical variables such as flow velocity (v), fluid viscosity (μ), fluid density (ρ) and characteristic dimension (L) (e.g. height) of the channel. It is well known that:

For relatively low values of Re, the fluid flow is laminar, characterized by smooth, constant fluid motion in which viscous forces dominate.

For relatively high values of Re, the fluid flow is turbulent (non-laminar), characterized by flow instabilities such as eddies and vortices, associated with a dominance of inertial forces.

The skilled artisan will therefore realize that, for a given fluid (ρ, μ), he can "tune" the occurrence/extent of turbulence effects by adjusting the velocity (v) of the fluid flow and/or the geometry of the flow (thus altering L). It will be well within the capability of the skilled artisan to choose a flow state that produces turbulence effects that are strong enough to remove dead zones/static boundary layers from the gap, but simultaneously not so strong as to excite the above-mentioned acoustic vibration in structures close to (or in) the gap, such as the window.

There are various flow geometries that can be implemented in the abovementioned gap. For example, viewing the gap through the window along the optical axis O of the objective lens, one might consider:

A lateral flow of gas in one direction, e.g. from left to right. Turbulence in this situation is then adjusted by varying the flow velocity.

Two opposing lateral flows of gas—one from the left, one from the right—that collide "head on" along an interposed diameter of the window. Turbulence will be generated in this case by virtue of the collision of the opposing gas streams, though the extent of such turbulence can still be adjusted by varying the flow velocity.

A generalization of the situation in the previous item, involving more than two inwardly directed lateral flows.

Two opposing lateral flows of gas—one from the left, one from the right—that do not collide "head on" but, instead, shear alongside one another (analogous to road traffic in opposite lanes). Here, the shearing motion at the interface between the flows generates turbulence, though the extent of such turbulence can still be adjusted by varying the flow velocity.

Etc.

However, the current inventors achieved particularly satisfactory results in an embodiment whereby the gas flow in the gap is directed so as to at least partially follow a substantially radial pattern outward from the window. Such a flow has the advantage that it intrinsically carries water vapor molecules away from the window. It is also a geometry that the inventors found to be less susceptible to excite acoustic vibration modes in the window. One way to produce such a flow pattern is to vertically administer the gas into the gap (i.e. in a direction parallel to the optical axis O of the objective lens), and then allow it to be deflected outward (in a range of lateral/radial directions, all perpendicular to O) as a natural result of the confined vertical extent of the gap. Such vertical administration could, for example, occur by feeding the gas into the gap through one or more upward-facing apertures in the sample holder, located so as to be relatively close to the optical axis O.

With reference to the discussion in the previous paragraph, the inventors have found that a particularly useful embodiment of the current invention is one in which:

The jacket comprises a series of gas apertures arranged along a periphery of the ELE;

The jacket encloses a gas passage between an inner surface of the jacket and an outer surface of the objective lens;

Said substantially dry gas is caused to pass through said gas passage and emerge from said apertures into said gap.

Such a configuration achieves a number of synergistic results. For example:

It provides a convenient way of achieving the abovementioned flow geometry, whereby gas flow in the gap is directed so as to at least partially follow a substantially radial pattern outward from the window. The gas is administered vertically from the objective side, which is generally easier than administering it from the sample side.

The use of a plurality of (relatively small) gas apertures—arranged along a circumferential path at the edge of the ELE—allows finer tuning of turbulence effects, since turbulence is now generated in a relatively "homogeneous" manner (small gas streams coming from many angles, rather than larger gas streams coming from just a few angles).

Administering the gas inside the jacket allows the gas to serve a double purpose, namely temperature control of the objective lens in addition to purging of the gap. It also helps to dissuade migration of water molecules into the jacket from the sample side.

In an example (which is purely given for illustration purposes, and should not be interpreted as limiting):

Eight holes are distributed at equal intervals around the circumference of the ELE, disposed along a circular path with a diameter of ca. 10 mm.

Each hole has a diameter (bore size) of ca. 0.3 mm.

If desired, the skilled artisan will be able to design and implement many variations of these parameters in order to suit the needs of a particular situation.

In a particular embodiment of the current invention, the window is comprised in the sample holder. For example, the sample can be located in a chamber having a wall that faces the ELE, whereby the wall contains an aperture into which the window is sealed (or whereby the entire wall itself is transparent). Such a set-up lends itself in particular to application in an inverted microscope, though it can also be employed in a non-inverted microscope.

By way of additional (non-limiting) example, the following indicative values can be used for guidance purposes:

The gap has a thickness in the range 0.2-0.3 mm;

The window has a thickness in the range 140-200 μm;

The velocity of the gas lies in the range 0.75-1.25 m/s.

Once again, adjustment/tailoring of these values to match the needs of a specific situation will be well within the abilities of the skilled artisan. For example, the skilled artisan may want to use a significantly thicker window (of the order of a few mm, for instance), and will be able to alter the optical design of the objective lens to cope with such a thicker window (which, for example, will imply a greater working distance, and will affect inter alia the numerical aperture (NA) of the objective lens).

In a particular embodiment of the current invention, the window is at least partially coated with a film of thermally impeding material (which may serve to impede radiative and/or conductive heat loss through the window, e.g. at least partially reflecting infrared radiation with a wavelength in the range 1-10 μm). Such an embodiment serves to further mitigate loss of heat from the objective lens through the window and towards the sample (which acts as a heat sink). The coating may be provided on either surface of the window, or on both surfaces, if so desired; alternatively, a film may be sandwiched between two layers of window material, thus forming a laminated structure. The thickness of the film may, for example, be of the order of a few tens of nanometers. The material chosen for the coating film may be intrinsically transparent (e.g. as in the case of a material such as silicon nitride), or it may be applied to the window in such a way as to behave in a (quasi-)transparent manner. As an example of the latter scenario, a thin "layer" of gold with a thickness of the order of about 50 nm will, in fact, comprise isolated islands of gold with intervening blank spaces; these islands are very effective at reflecting back infrared wavelengths (e.g. ca. 99% efficient), whereas the blank spaces allow visible light to substantially pass (e.g. ca. 90% transmission).

In an embodiment of the invention, the jacket (around the objective lens) comprises a material selected from the group comprising ceramic materials, vitreous materials, plastics, resins, and combinations hereof. The jacket may have a simple structure (comprising only one material) or a compound structure (comprising a plurality of materials); for example, it might have a sandwiched composition comprising layers of different materials, or a matrix composition in which particles or fibers of one material are embedded in a bulk carrier of another material. It may be manufactured by whatever method is convenient for the material(s) and shape concerned, e.g. via injection molding, casting, milling, etc. The jacket may be a relatively tight fit or a looser fit around the objective, depending on the dictates of a particular situation. It may also entirely encapsulate the objective lens, or just partially encapsulate it. Needless to say, the jacket may not obstruct the ELE/optical axis of the objective lens, e.g. it may contain an aperture with a seam that fits snugly around the ELE.

In another embodiment of the invention, the abovementioned window comprises a material selected from the group comprising vitreous materials, quartz, calcium fluoride, polymers (e.g. polycarbonate), and combinations hereof. It will ideally be optically flat, and exhibit (essentially) no optical power. It may have various shapes, e.g. circular, polygonal, square, etc. It may comprise a single material or be a composite structure of several materials, e.g. with a laminated/sandwich composition. It may be mounted in place (e.g. attached to the sample holder) using various means, such as gluing, sealing with rubber, pressing against a washer, etc. The skilled artisan will be able to choose a suitable thickness for the window, depending inter alia on its composition, diameter, etc. In many practical situations, a window with a width of the order of about 1-2 cm should give satisfactory results.

In yet another embodiment of the invention, the aforementioned gas is selected from the group comprising air, nitrogen, the noble gases, and combinations hereof. The gas may be intrinsically dry (e.g. because it is bottled by a supplier as such) and/or it may be dried by passing it through a dessicating device. It may, for example, be supplied to the abovementioned gap at a temperature at or near room temperature (ca. 300 K), but it can also be supplied at a lower temperature; for instance, one could use dry vapor from liquid nitrogen as a purge gas. The skilled artisan will appreciate that the volume of gas supplied to the gap per unit of time should not be such as to substantially increase the temperature of the sample.

The term "substantially dry" as used with reference to the gas should be interpreted as indicating that it has a relative humidity of at most 10%, preferably less than 5%, and ideally less than 1%. Particularly satisfactory results are achieved with a relative humidity value less than 0.1%.

The invention will now be elucidated in more detail on the basis of exemplary embodiments and the accompanying schematic drawings, in which.

In the Figures, where pertinent, corresponding parts are indicated using corresponding reference symbols.

EMBODIMENT 1

Figure 1:
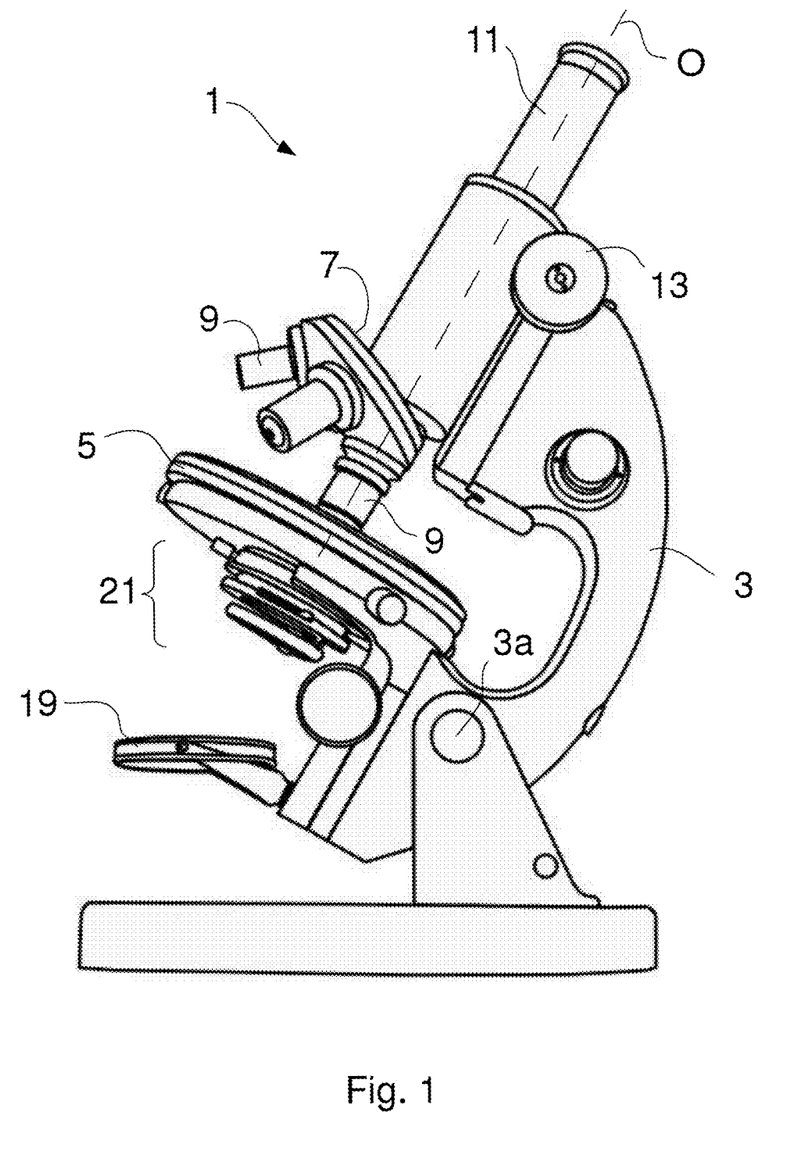
FIG. 1 renders a perspective view of an embodiment of an optical microscope, of a type in which the current invention can be applied.

FIG. 1 renders a perspective view of an embodiment of an optical microscope 1, of a type in which the current invention can be applied. The depicted microscope 1 is of a relatively simple type, but it is sufficient to illustrate the main parts and operating principle of such an instrument. The skilled artisan will be aware that more sophisticated designs of such microscopes are commercially available.

The microscope 1 depicted in FIG. 1 is of a standard, "non-inverted" type. As stated above, the invention can also be applied in microscopes of an "inverted" type. An example of this latter type of microscope will be discussed later with regard to FIG. 4.

The microscope 1 comprises a frame 3 on which various parts and sub-assemblies are mounted. These include a sample holder 5 and a turret 7 that carries various objective lenses 9. By rotating the turret 7, different ones of these objective lenses 9 can be moved into position along an optical axis O. Also disposed along the optical axis O is an ocular 11, which may be replaced by a camera, if desired. A focusing mechanism 13 can be used to bring a selected objective lens 9 into a focus position with respect to a sample S, which is held on the sample holder 5 with the aid of a clamping mechanism 15 (see FIG. 2). In the current example, the focusing mechanism 13 is a rack and pinion mechanism that can slide the entire column 7, 9, 11 longitudinally along the direction of the optical axis O; however, other mechanisms are possible, and may (for example) involve motion of the sample holder 5 instead of (or in addition to) the column 7, 9, 11 (or parts thereof). The skilled artisan will be familiar with such variants. Disposed in a middle region of the sample holder 5, proximal the optical axis O, is an aperture 17 (see FIG. 2), which allows light from an illuminator 19 to pass through the sample holder 5 and illuminate the sample S from beneath. In the current example, the illuminator 19 is an adjustable mirror that can be used to direct ambient light along the optical axis O, but it may alternatively comprise an electric lamp, for example. Between the illuminator 19 and the sample holder 5 is an assembly 21 of various (optional) components, such as a condenser lens, polarization filter, etc. As here depicted, the optical axis O is canted at an angle to the vertical direction; however, if desired, this canting stance can be adjusted by rotating the frame 3 about pivot point 3a, whereby the optical axis O can be made vertical, if required (which may, for example, be desirable in situations in which there is a liquid in the sample holder 5).

Figure 2:
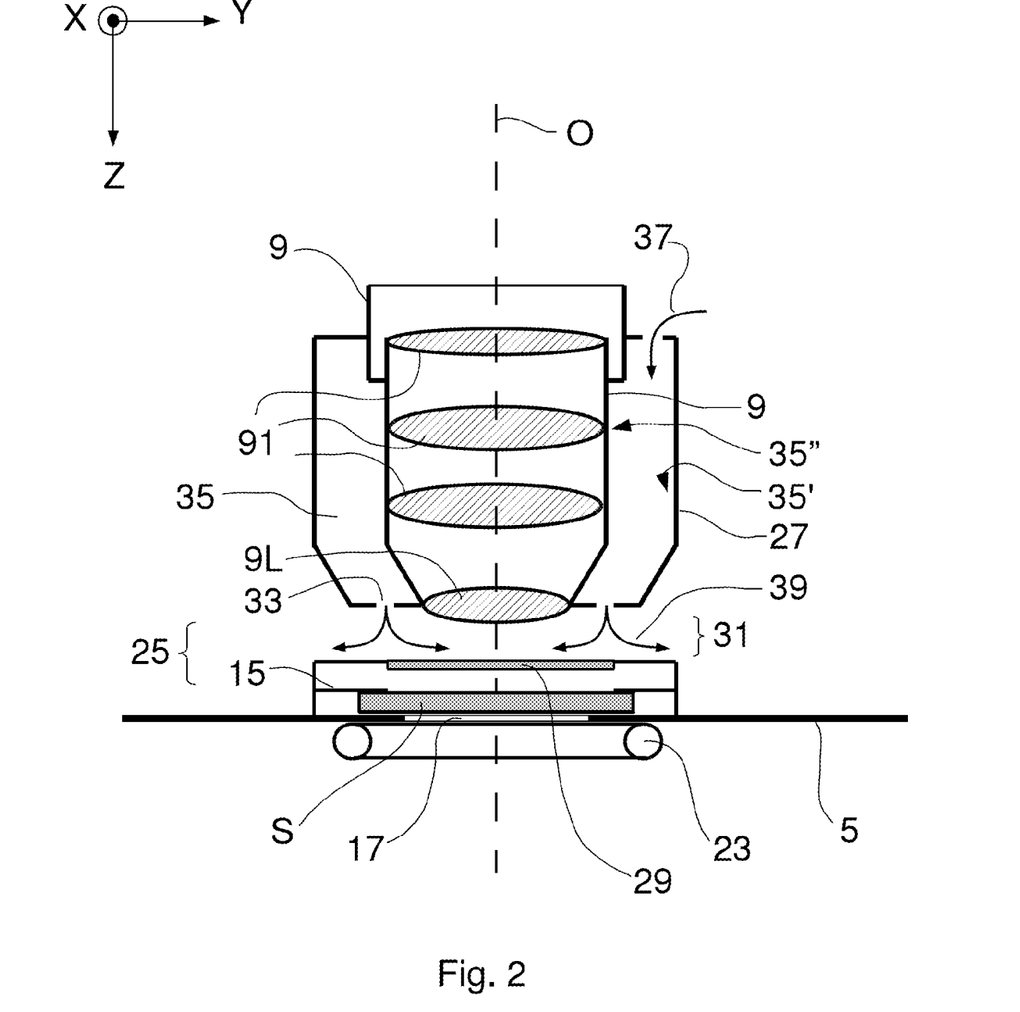
FIG. 2 renders a longitudinal cross-sectional view of part of an optical microscope as depicted in FIG. 1.

If the sample S is to be maintained at a low temperature (T<273 K) while it is being studied upon the sample holder 5, then the sample holder 5 will generally be provided with some sort of cooling construction 23 (see FIG. 2). As here depicted, this cooling construction 23 takes the form of a hollow conduit that is in intimate thermal contact with (the underside of) the sample holder 5 and through which a coolant such as liquid nitrogen (for example) can be caused to flow; however, the skilled artisan will realize that such a construction 23 can have many variants and/or alternatives, e.g. making use of a Peltier cooling element, for instance.

Turning now in more detail to the objective lens 9 depicted in FIG. 2 (which is not to scale), the illustrated lens 9 is a compound lens with a plurality of individual lens elements 91. Of particular interest here is the ELE (extremal lens element) 9L, which is the lens element closest to the sample S. Between this ELE 9L and the sample S is an intervening space 25, which will generally have a height (parallel to the depicted Z axis) of the order of about a millimeter. Because of this close proximity across said relatively shallow intervening space 25, a cooled sample S can have adverse effects on (at least) the ELE 9L, such effects including the condensation of water vapor and/or ice formation on (at least) the ELE 9L, and/or a strong cooling of (at least) the ELE 9L, with an attendant substantial change in its optical properties.

Figure 3:
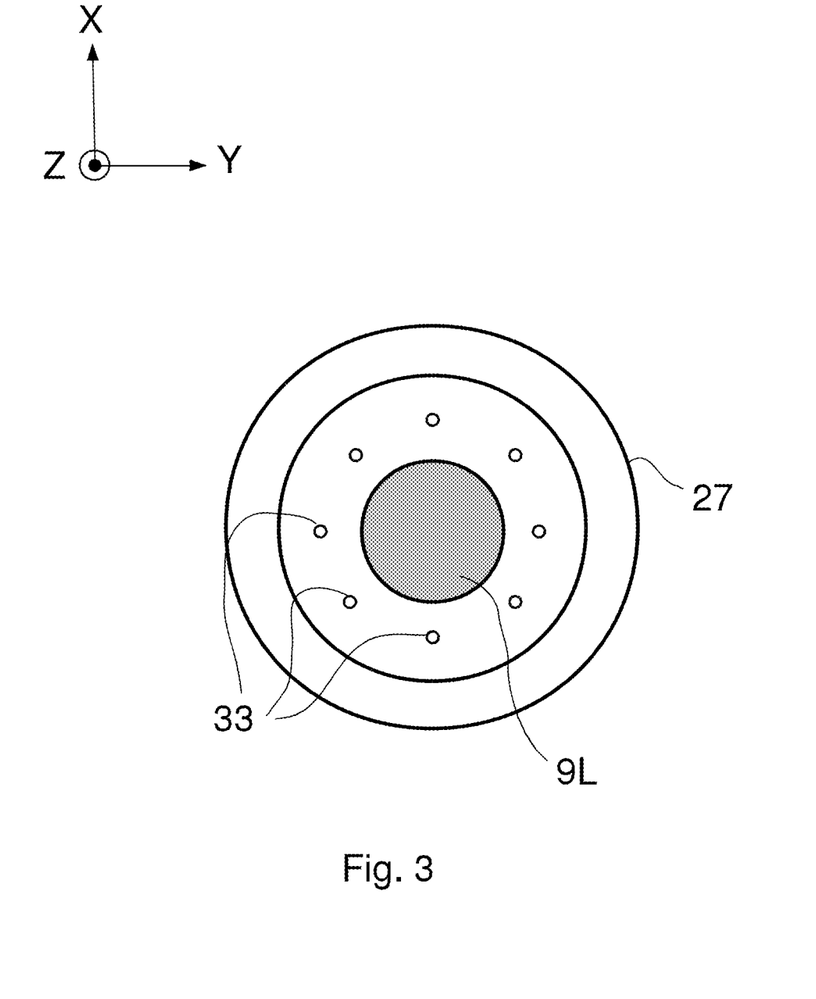
FIG. 3 shows part of the subject of FIG. 2 when viewed from beneath.

The invention addresses these problems by providing the objective lens 9 in a thermally insulating jacket 27, and by providing a transparent window 29 in the intervening space 25 between the ALE 9L and the sample S. In the depicted set-up, the window 29 is attached to the sample holder 5, as part of a chamber enclosing the sample S, and defines a gap 31 between the window 29 and the ELE 9L. The invention provides a flow of substantially dry gas in this gap 31. As set forth above, this flow may be realized in many different ways, but the particular set-up depicted in FIGS. 2 and 3 achieves a specific flow geometry in the following manner:

The jacket 27 comprises a series of gas apertures 33 arranged along a periphery of the ELE 9L;
The jacket 27 comprises a gas passage 35 between an inner surface 35' of the jacket 27 and an outer surface 35" of the objective lens 9;
The substantially dry gas is caused to pass through the gas passage 35 and emerge from the apertures 33 into the gap 31.

To this end, an input stream 37 of said gas is pumped under pressure into the passage 35. It should be noted that the passage 35 can take many other possible forms: for example, if desired, the inner surface 35' of the jacket 27 and the outer surface 35" of the objective lens 9 may be in (more) intimate contact with each other, and the passage 35 may take the form of a (spiral) bore created (e.g. machined, molded or cast) in the inner surface 35' of the jacket 27. It should also be noted that, although the jacket 27 is depicted here as having a simple wall structure (a uniform wall of insulating material), it may (if desired) instead have a compound wall structure, e.g. comprising an insulator material (or insulator cavity) sandwiched between inner and outer wall portions. The skilled artisan will grasp these points and be able to contrive many possible variations thereof within the scope of the appended claims.

As the gas emerges (substantially parallel to Z) from the apertures 33 it will collide with a top surface of the window 29 (and/or a wall in which said window is located) and splay into a horizontal flow (parallel to the XY plane), as indicated by arrows 39. Part of this splayed flow 39 will be directed inward (towards O), and part of it will be directed (radially) outward (away from O). The inward-directed parts of the flow from the various apertures 33 will collide and create a turbulent environment above the window 29. For a given gas, the extent of this turbulence will be influenced inter alia by:

The width of the gas apertures 33;
The velocity of the gas as it emerges from the apertures 33—which, in turn, will depend inter alia on the pressure of the input stream 37 and the geometry of the passage 35.

According to the invention, this turbulence should be strong enough to deter formation/stability of dead zones in the gap 31, but not so strong as to excite (substantial) acoustic resonance of the window 29 (and, possibly, of the sample S and/or (parts of) the sample holder 5).

As depicted in FIG. 3, the gas apertures 33 of this particular embodiment are disposed at equal (one eighth) intervals along the (circular) circumference of the ELE 9L; however, this does not have to be the case, and many other pluralities/geometries are conceivable.

As an extra measure to improve thermal isolation of the objective lens 9 from the cold sample S and sample holder 5, one may at least partially coat the window 29 with a film of thermally impeding (substantially transparent) material (not depicted); in fact, if so desired, such a film may be provided on both major surfaces of the window 29.

As regards certain specific aspects of the illustrated/discussed embodiment, the following examples can be given:

The jacket 27 comprises a thermoplastic such as polypropylene, which is manufactured with the aid of an injection molding technique.
The window 29 comprises quartz, with a diameter of 10 mm and a thickness of 170 μm.
The gas apertures 33 disposed around the circumference of the ELE 9L have a diameter (bore size) of 0.3 mm, and are located on a circular locus with a diameter of 10 mm.
The gap 31 has a height (along the Z axis) of 0.3 mm, and is purged using dry nitrogen at a flow rate of 1 m/s.

EMBODIMENT 2

Figure 4:
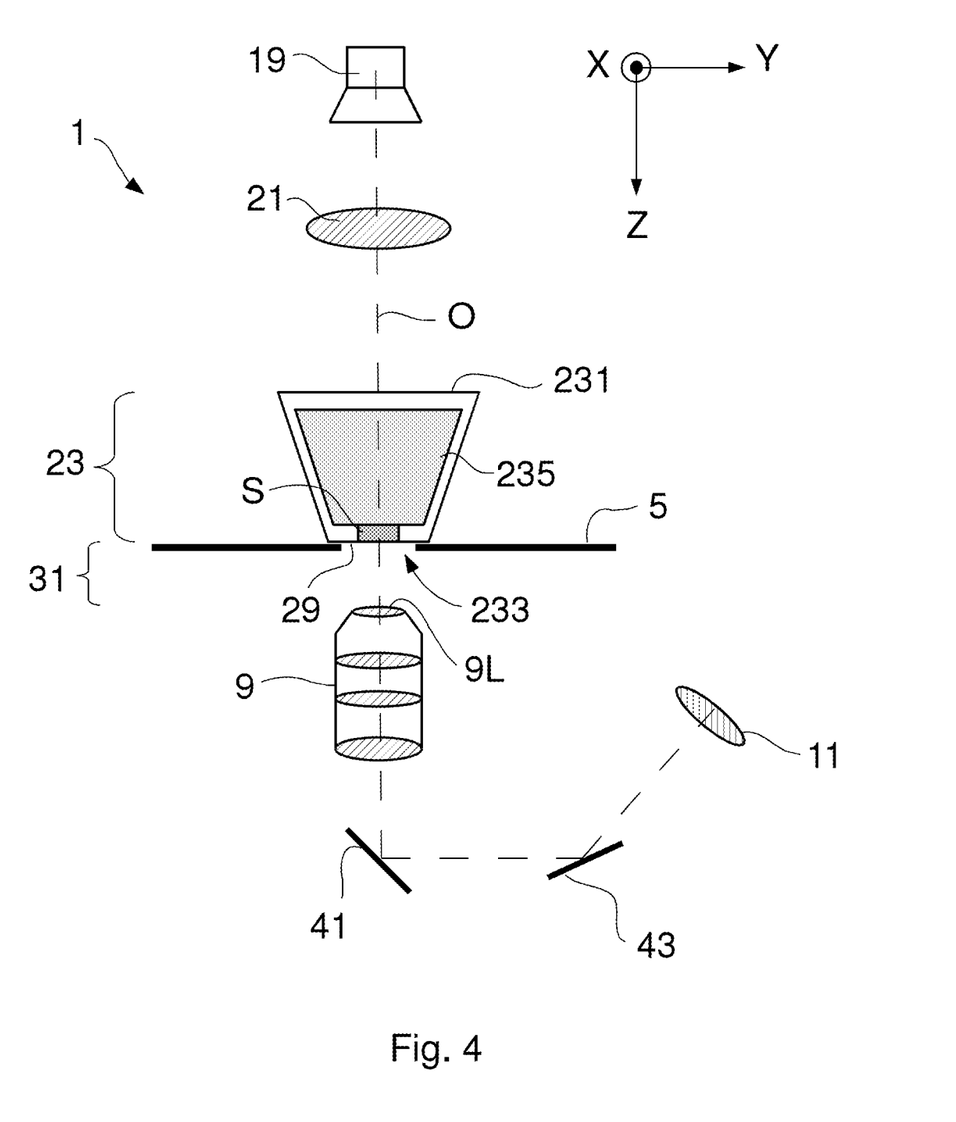
FIG. 4 renders a longitudinal cross-sectional depiction of the structure and operation of an inverted microscope in which the current invention can be applied.

FIG. 4 comprises similar components to those of FIG. 1, except that it operates in an inverted configuration, meaning that the objective lens 9 is located below the sample holder 5 rather than above it (when viewed along the optical axis O/parallel to the Z-axis). As here illustrated, the cooling construction 23 takes a different form to that depicted in FIG. 2, in that it comprises a chamber (container/vessel) 231 with a bottom wall 233 in which is located a window 29. A vessel 235 with thermally conductive walls is in intimate thermal contact with the sample S, and is at least partially filled with a coolant, such as liquid nitrogen; in this way, the vessel 235 acts as a heat sink, drawing heat away from the sample S and serving to lower its temperature. The sample S rests on (or very near) the window 29, and can be viewed through it from beneath. Also shown are mirrors 41, 43 which serve to bend the optical axis O into a direction that allows comfortable viewing through the eyepiece 11.

In accordance with the invention, the objective lens 9 can be provided with a jacket 27, and a flow 39 of substantially dry gas can be provided in a gap 31 between the window 29 and the ELE 9L; see, in this regard, FIG. 2, and rotate its contents through 180° about the depicted X-axis.

The invention claimed is:

1. A method of studying a sample using an optical microscope, comprising the following steps:
   providing the sample in a sample holder comprising means to maintain the sample at a temperature T below 273 K;
   providing a microscope objective lens having an extremal lens element proximal the sample holder, the objective lens in a thermally insulating jacket;
   bringing the lens into a focus position proximal the sample, the extremal lens element and sample being separated by an intervening space;
   providing a transparent window in said intervening space, with a gap between the window and the extremal lens element and a gap between the between the window and the sample;
   providing a flow of substantially dry gas in said gap between the window and the extremal lens element; and
   tailoring the geometry and velocity of said flow so that, at least in said gap, the flow:
      is non-laminar; and
      does not excite substantial acoustic vibration in a structure proximal the gap;
   wherein the gap between the window and the extremal lens element has a thickness in the range 0.2-0.3 mm;
   the window has a thickness in the range 140-200 μm; and
   the velocity of the gas lies in the range 0.75-1.25 m/s.

2. The method according to claim 1, wherein said structure is at least one of:
   the window;
   the sample;
   the sample holder.

3. The method according to claim 1, wherein said flow is directed so as to at least partially follow a substantially radial pattern outward from the window.

4. The method according to claim 3, wherein:
   the jacket comprises a series of gas apertures arranged along a periphery of the extremal lens element;
   the jacket encloses a gas passage between an inner surface of the jacket and an outer surface of the objective lens;
   said substantially dry gas is caused to pass through said gas passage and emerge from said apertures into said gap.

5. The method according to claim 1, wherein the window is comprised in the sample holder.

6. The method according to claim 1, wherein the window is at least partially coated with a film of thermally impeding material.

7. The method according to claim 1, wherein the jacket comprises a material selected from the group comprising ceramic materials, vitreous materials, plastics, resins, and combinations hereof.

8. The method according to claim 1, wherein the window comprises a material selected from the group comprising vitreous materials, quartz, calcium fluoride, polymers, and combinations hereof.

9. The method according to claim 1, wherein the gas is selected from the group comprising air, nitrogen, the noble gases, and combinations hereof.

10. An optical microscope constructed and arranged to perform a method as claimed in claim 1.

11. An optical microscope, comprising:
    a sample holder for holding a sample, the sample holder having a cooler for maintaining the sample at a temp T below 273K;
    a microscope objective lens having an extremal lens element proximal to the sample holder, the objective lens positioned in a thermally insulating jacket, the jacket comprising a series of gas apertures arranged along a periphery of the extremal lens element, the extremal lens element and the sample being separated by an intervening space; and
    a transparent window in said intervening space, with a gap between the window and the extremal lens element, the series of gas apertures configured for passing through substantially dry gas into said gap, the flow of said gas being non-laminar and not exciting substantial acoustic vibration in a structure proximal the gap;
    the gap between the window and the extremal lens element has a thickness in the range 0.2-0.3 mm;
    the window has a thickness in the range 140-200 μm;
    the velocity of the gas lies in the range 0.75-1.25 m/s.

12. The optical microscope of claim 11 in which said structure is at least one of:
    the window;
    the sample;
    the sample holder.

13. The optical microscope of claim 11, wherein the window is comprised in the sample holder.

14. The optical microscope of claim 11, wherein the window is at least partially coated with a film of thermally impeding material.

15. The optical microscope of claim 11, wherein the jacket comprises a material selected from the group comprising ceramic materials, vitreous materials, plastics, resins, and combinations hereof.

16. The optical microscope of claim 11, wherein the window comprises a material selected from the group comprising vitreous materials, quartz, calcium fluoride, polymers, and combinations hereof.

17. The optical microscope of claim 11, further comprising a source of a gas selected from the group comprising air, nitrogen, the noble gases, and combinations hereof.

* * * * *